(12) United States Patent
Pisharodi

(10) Patent No.: US 10,835,293 B2
(45) Date of Patent: Nov. 17, 2020

(54) MULTI-AXIS INTERNAL SPINAL FIXATION

(71) Applicant: Perumala Corporation, Brownsville, TX (US)

(72) Inventor: Madhavan Pisharodi, Brownsville, TX (US)

(73) Assignee: Perumala Holdings, LLC, Brownsville, TX (US)

(*) Notice: Subject to any disclaimer, the term of this patent is extended or adjusted under 35 U.S.C. 154(b) by 8 days.

(21) Appl. No.: 16/148,820

(22) Filed: Oct. 1, 2018

(65) Prior Publication Data

US 2019/0099205 A1     Apr. 4, 2019

Related U.S. Application Data

(60) Provisional application No. 62/566,991, filed on Oct. 2, 2017.

(51) Int. Cl.
*A61B 17/70*     (2006.01)
*A61B 17/80*     (2006.01)
(Continued)

(52) U.S. Cl.
CPC ...... *A61B 17/7059* (2013.01); *A61B 17/7043* (2013.01); *A61B 17/8023* (2013.01);
(Continued)

(58) Field of Classification Search
CPC ............ A61B 17/7043; A61B 17/7007; A61B 17/7041; A61B 17/7058; A61B 17/7059; A61B 17/8023; A61B 2017/564; A61B 2090/037; A61F 2002/30433; A61F 2002/30622; A61F 2002/3069; A61F 2/4455
See application file for complete search history.

(56) References Cited

U.S. PATENT DOCUMENTS 5,084,049 A    1/1992  Asher
5,707,372 A    1/1998  Errico
(Continued)

FOREIGN PATENT DOCUMENTS

WO     1994020048     9/1994

OTHER PUBLICATIONS

Elgafy et al, "Rationale of Revision Lumbar Spine Surgery", Jan. 12, 2012.
(Continued)

*Primary Examiner* — Samuel S Hanna
(74) *Attorney, Agent, or Firm* — D'Ambrosio & Menon, PLLC; Usha Menon

(57) ABSTRACT

According to an embodiment, a spinal implant having vertical and horizontal plates with through-holes for receiving a pre-configured square bolt is disclosed. The embodiments of the invention include very long square bolts that can accommodate the height of at least of two vertically stacked plates. When used to reduce spondylolisthesis, a portion of the square bolt can be broken after the desired alignment of the listhetic vertebrae is observed. The square bolts also allow extension of vertical plates above or below an existing fusion by placement of an extension vertical plate on to the previous one without removing it. This makes extension of instrumentation extremely easy.

5 Claims, 3 Drawing Sheets

(51) Int. Cl.
*A61F 2/44* (2006.01)
*A61B 90/00* (2016.01)
*A61F 2/30* (2006.01)
*A61B 17/56* (2006.01)

(52) U.S. Cl.
CPC ........ *A61F 2/4455* (2013.01); *A61B 17/7007* (2013.01); *A61B 17/7041* (2013.01); *A61B 17/7058* (2013.01); *A61B 2017/564* (2013.01); *A61B 2090/037* (2016.02); *A61F 2002/3069* (2013.01); *A61F 2002/30433* (2013.01); *A61F 2002/30622* (2013.01)

(56) References Cited

U.S. PATENT DOCUMENTS

| | | |
|---|---|---|
| 6,355,038 B1 | 3/2002 | Pisharodi |
| 6,669,697 B1* | 12/2003 | Pisharodi ............ A61B 17/7007 606/250 |
| 7,887,568 B2 | 2/2011 | Ahlgren |
| 2001/0016742 A1 | 8/2001 | Rogozinski |
| 2006/0084980 A1* | 4/2006 | Melkent ............. A61B 17/7007 606/281 |
| 2006/0271052 A1 | 11/2006 | Stern |
| 2007/0270820 A1 | 11/2007 | Dickinson |
| 2013/0218208 A1 | 8/2013 | Khoury |
| 2015/0100089 A1 | 4/2015 | Richelsoph et al. |

OTHER PUBLICATIONS

International Search Report and Written Opinion dated Dec. 10, 2018 issued for co-pending related PCT Patent App. No. PCT/US2018/053790.

* cited by examiner

1 - original fusion
2 - extension of fusion

MULTI-AXIS INTERNAL SPINAL FIXATION

CROSS-REFERENCE TO RELATED APPLICATION

This application claims priority from U.S. Provisional Patent Application No. 62/566,991 filed on Oct. 2, 2017, the entire disclosure of which is part of the disclosure of the present application and is hereby incorporated by reference in its entirety.

BACKGROUND AND FIELD OF THE INVENTION

This invention relates generally to multi-axis internal spinal fixation.

There are many systems available for internal fixation of the spine. A problem with all such systems, however, is the joint between the screws used to affix the system to the pedicle and the rods, cross-bars, and/or plates of the system. The problems at the site of this linkage may result from the geometry of the joint between the screw and the rod or plate. This difficult geometry results from several factors, including the different angles and placement of the vertebrae and their relative sizes, the shape of the vertebrae and the spacing between vertebrae, the placement of the screws, the lordosis of the spine, and the need to insert the screws into each vertebra at an angle. With regard to the angle of the pedicle screws, pedicle screws are angled inwardly and upwardly into the vertebra for maximum strength and, because the surfaces of the pedicles of each vertebrae are angled relative to each other, the screws rarely line up across the vertebral body into which they are screwed. Nor do they line up from one vertebra to the adjacent vertebra even if the adjacent vertebrae are the same size and shape (which they generally are not). Because the pedicle screws do not line up, the rod which runs along the longitudinal axis of the patient's spinal column, which provides the structural rigidity required to stabilize the spine, must either be bent to the location of each screw head or the stabilizer must be provided with adjustable structure which enables the screw head to be attached to the rod.

U.S. Pat. Nos. 6,355,038 and 6,669,697, the contents of which are incorporated by reference herein in its entirety, disclose a spinal stabilizer system comprising a rod, a screw, a cross-bar/plate having a hole therein, means for attaching the cross-bar to the rod, and a washer. The washer comprises a cylindrical body having one end angled with respect to the side walls of the cylindrical body and a longitudinal passage therethrough for receiving the screw for affixing the cross-bar to the vertebra of a patient. The washer also comprises means for resting on and rotatably engaging the margins of the hole in the cross-bar so that the body is capable of being rotated in the hole in the cross-bar to provide an infinite variety of angles and pedicle screw placements while maintaining an optimal interface between the head of the screw and the washer so as to effectively transfer the load from the spinal column to the cross-bar.

The spinal stabilizer system disclosed in U.S. Pat. Nos. 6,355,038 and 6,669,697 has several advantages. However, the inventor observed that the rods (or vertical plates) disclosed therein were subject to breakage when there was excess stress as in obesity, acute curvatures of the spine, and while reducing spondylolisthesis. Increasing the thickness of the vertical plates was proposed as a solution. However, an increase in the plate thickness adversely affected the bendability of the plates thereby making them unsuitable for their intended purpose.

Accordingly, there is a need for a spinal implant wherein the vertical plates can be bent and do not break under stress or tension.

SUMMARY OF THE INVENTION

According to an embodiment, a spondylolisthesis reduction kit is provided. The spondylolisthesis reduction kit contains: a plurality of horizontal plates; a plurality of vertical plates, and two sets of bolts. A first set of bolts is configured to couple one or more stacked pairs of vertical plates to a first horizontal plate. Each of the bolts in the first set of bolts includes: a square-shaped head, a non-threaded portion proximal to the square-shaped head, a first threaded portion proximal to the non-threaded portion, a second threaded portion, and a waist portion. The waist portion is configured to separate the first and second threaded portions. The second threaded portion is configured to be broken off. The combined length of the non-threaded portion and the first threaded portion is about 17.1 mm or longer (for example, when more than two vertical plates are stacked, the threaded portion can be longer than 17.1 mm).

The kit further includes a second set of bolts, wherein the second set of bolts is substantially shorter in length than the first set of bolts. the second set of bolts is configured to couple the one or more stacked pairs of vertical plates to at least a second horizontal plate, wherein each of the second set of bolts includes: a square-shaped head, a non-threaded portion proximal the square-shaped head, and a threaded portion proximal the non-threaded portion. The combined length of the non-threaded portion and the threaded portion of each of the second set of bolts is approximately 17.1 mm or longer. Each horizontal and vertical plate includes a through-hole for receiving one or more bolts from the first or second set of bolts.

According to another embodiment, a spinal implant kit is provided. The spinal implant kit contains: a plurality of horizontal plates; a plurality of vertical plates; and a set of bolts. Each of the bolts includes: a square-shaped head, a non-threaded portion proximal the square-shaped head, and a threaded portion proximal the non-threaded portion. Each horizontal and vertical plate includes a through-hole for receiving one or more bolts. The combined length of the non-threaded portion and the threaded portion is approximately 17.1 mm. The bolts are configured to couple one or more pairs of vertical plates to two or more horizontal plates. The spinal implant comprises a biocompatible material. In one embodiment, the biocompatible material comprises titanium.

In another embodiment, a method for extending an original spinal fusion is provided. The original spinal fusion comprises two or more horizontal plates and a first set of vertical plates coupled to the two or more horizontal plates. Extending the original spinal fusion involves: positioning a second set of vertical plates over the first set of vertical plates; affixing the second set of vertical plate to the first set of vertical plate and a last horizontal plate in the original spinal fusion; and coupling the second set of vertical plates to an additional horizontal plate or horizontal plates. The method further comprises providing a set of bolts. Each of the bolts possesses a pre-determined length for affixing the second set of vertical plates to the first set of vertical plates.

In yet another embodiment, a method of facilitating spondylolisthesis reduction is disclosed. The method involves providing a spinal implant kit containing a plurality of horizontal and vertical plates and two sets of bolts. Each of the plates includes a through-hole for receiving a bolt. The method further involves stacking a first vertical plate over a second vertical plate and a third vertical plate over a fourth vertical plate. Using a first set of bolts, the stacked vertical plates are secured to at least one horizontal plate. The horizontal plate can be positioned along a perpendicular axis to the stacked vertical plates. The method further involves using a second set of bolts to secure the stacked vertical plates to another horizontal plate, wherein this additional horizontal plate is positioned along a lower plane than the first horizontal plate for listhesis reduction. The second set of bolts is substantially longer than the first set of bolts. Each of the stacked vertical plates is configured to be bent to a desired degree of lumbar lordosis before affixing it to the horizontal plates. The method further comprises lifting a listhetic vertebrae upwards and back into normal alignment by forcing the stacked vertical plates down onto the listhetic vertebrae. Each of the second set of bolts includes a breakable portion. After alignment of the listhetic vertebrae, the breakable portion is detached. The vertical and horizontal plates and the first and second sets of bolts are each made of a biocompatible material.

BRIEF DESCRIPTION OF THE DRAWINGS

The features and advantages of certain embodiments will be more readily appreciated when considered in conjunction with the accompanying figures. The figures are not to be construed as limiting any of the preferred embodiments.

DETAILED DESCRIPTION OF THE INVENTION

Contemplated embodiments disclosed herein address the deficiencies of the prior art that was discussed earlier. The embodiments of the invention also disclose methods for extending spinal fusion without removing the existing instrumentation.

Figure 1A:
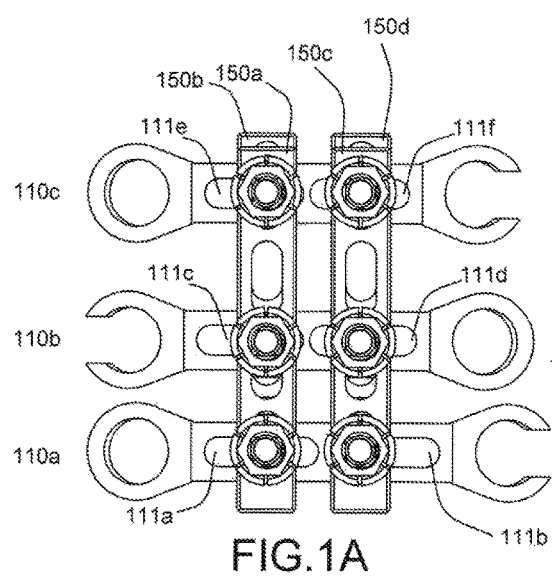
FIGS. 1A and 1B illustrate a spinal implant in accordance with one embodiment of the invention.
Figure 1C:
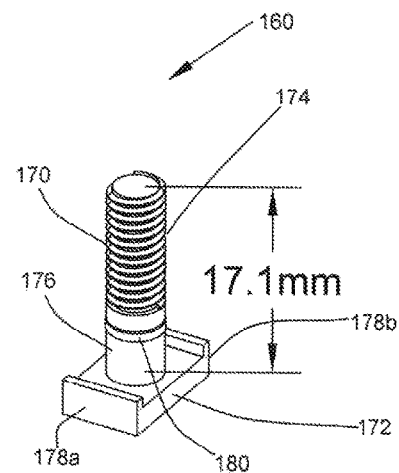
FIG. 1C illustrates an embodiment of a square bolt in accordance with one embodiment of the invention.
Figure 1B:
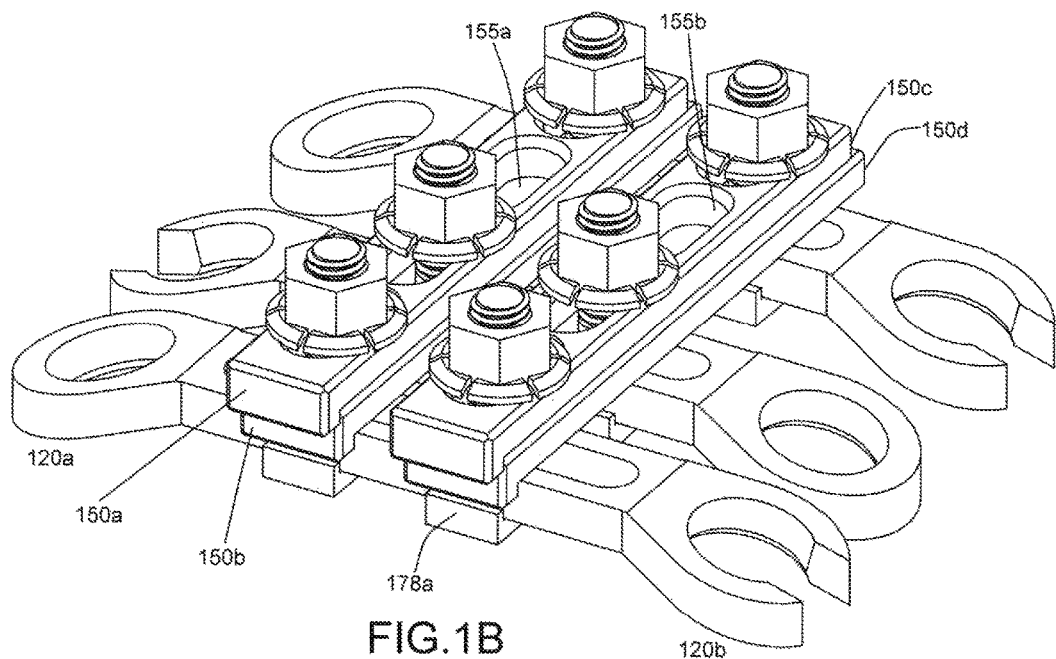

An embodiment of a spinal implant constructed in accordance with the present invention is shown in FIGS. 1A and 1B. The embodiment, indicated generally at reference numeral 100, includes horizontal plates 110a-c ("110"). Each of the horizontal plates 110a-c includes a pair of oval through-holes 111a-b, 111c-d, and 111e-f ("111") respectively. The through-holes are intermediate the ends 120a-b, 120c-d and 120e-f ("120") of each horizontal plate 110a-c respectively. In an embodiment, a horizontal plate is bent at the ends 120a, 120b. The bent ends serve several advantages other than accommodating the shape of the vertebral body and is therefore particularly adapted for use in the spinal implant of the present invention.

The implant 100 further includes vertical plates 150a-d ("150"). Each of the vertical plates 150 is also provided with one or more oval through-holes 155a and 155b. The vertical plates 150 are oriented along the longitudinal axis of the spinal column on either side of the midline of the vertebrae (not shown).

Square bolts 160a-160f (together "160") are provided to secure the vertical plates to the horizontal plates. An exemplary square bolt of the invention is illustrated in FIG. 1C. The square bolt 160 includes a post 170 and a square-shaped head 172. The post 170 includes a threaded portion 174 and a non-threaded portion 176. Unlike the conventional bolts disclosed in the prior art which have a shorter length, typically around 12.1 mm, the square bolts 160 are around 35%-45% longer. In one embodiment, the length of the square bolt is around 17.1 mm. The square-shaped head 172 further includes an opposing pair of protrusions 178a,b ("178"). The protrusions 178 are dimensioned so that they can engage the outside edges of each horizontal plate 110. A nut 140 can be threaded onto the post 170 of square bolt 160 and tightened. In certain embodiments, the non-threaded portion 176 of the square bolt may include a belt-like protuberance 180 which can function to retain the square bolt in a groove of the through-holes 111a-f of the horizontal plates without the square bolt falling out of the horizontal plate 110a-c. The square bolt 160 is configured to be slidably moved within the through-holes 111a-f of the horizontal plates.

A method of facilitating spinal stabilization involves providing the spinal implant 100. In the operating theater, the vertical plates are secured to the horizontal plates. The vertical plate 150a is stacked over vertical plate 150b and vertical plate 150c is stacked over vertical plate 150d. The first pair of stacked vertical plates 150a-b is placed over the horizontal plates 110a-c proximal to the end 120a. The second pair of stacked plates 150c-d is placed over the horizontal plates 110a-c proximal to the end 120b. The first and second pair of stacked plates are positioned parallel to each other over the horizontal plates. The through-holes of the vertical plates are positioned above the through-holes of the horizontal plates forming a contiguous opening for the bolt 160. Each of the stacked vertical plates is configured to be individually bendable. In some embodiments, there maybe additional pairs of vertical plates next to 150a-b and 150c-d respectively.

The square bolts are configured to slide along the through-holes 111a-f of the horizontal plates to form a straight line to accommodate the straight vertical plates. Each of the stacked vertical plates can be bent to a desired degree of lumbar lordosis before affixing it to the horizontal plates.

A square bolt 160a is pushed upward from the base of a through-hole in the horizontal plate 110a. The non-threaded portion 176 of the square bolt is retained within the through-holes of the horizontal plate and the through-holes of a first pair of stacked vertical plates 150a-b. The threaded portion 174 of each square bolt passes upwardly through the through-holes of the horizontal and stacked vertical plates where it can be secured with the nut 28 and tightened. Similarly, the remaining square bolts 160b-f are pushed or pressed into the horizontal plates to securely couple the vertical stacked plates to the horizontal plates. The protrusions 178 of each square bolt is dimensioned so that they can engage the outside edges of each horizontal plate to prevent relative rotation between the square bolt 160 and the horizontal plate so that the nut 28 can be threaded onto the post 170 of square bolt 160 and tightened.

The square bolts have the extra length to accommodate two or more stacked plates. The extra-long square bolts ensure that the stacked vertical plates are securely coupled to the horizontal plates. The stacking of the vertical plates facilitates strengthening of the spinal implant without compromising on its ability to maintain spinal curvature, through the bendability of an individual vertical plate.

The square bolts, horizontal plates and vertical plates can be comprised of a resilient, biocompatible material that allows passage of the square bolt upwardly through oval through-holes in the horizontal plate and stacked vertical plates but resists passage back in the other direction so that the square bolt does not fall out of the through-holes. In some embodiments, the square bolts, horizontal plates and vertical plates may be made of titanium.

Figure 2B:
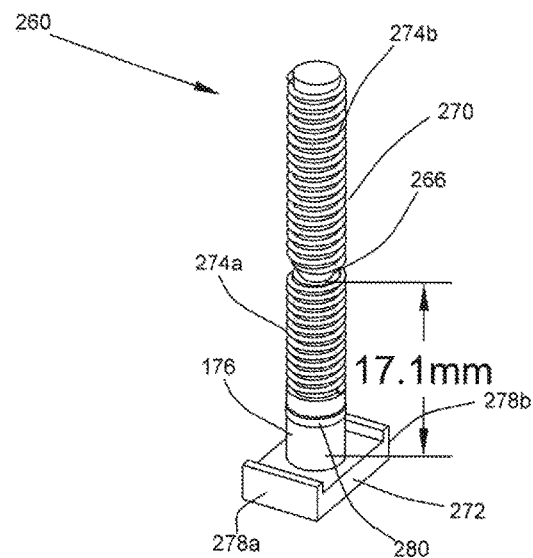
FIG. 2B illustrates an embodiment of a square bolt for reducing spondylolysthesis in accordance with one embodiment of the invention.
Figure 2A:
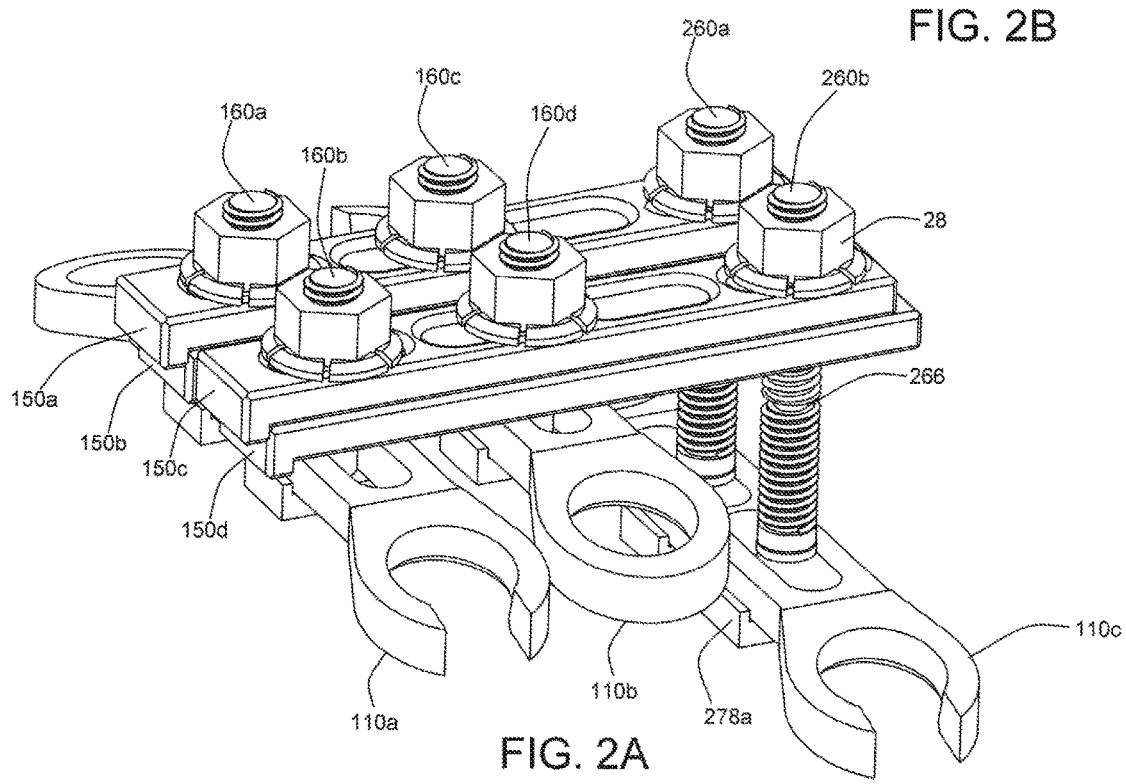
FIG. 2A illustrates a spinal implant for reducing spondylolysthesis in accordance with another embodiment of the invention.

Another embodiment of a spinal implant constructed in accordance with the present invention is shown in FIG. 2A. The second embodiment, indicated generally at reference numeral 200, can be used to reduce spondylolisthesis. The second embodiment 200 also includes horizontal plates 110 and vertical plates 150 as described with reference to FIGS. 1A and 1B. The features of the horizontal and vertical plates are as disclosed earlier and, are therefore, not repeated herein for brevity.

A first set of square bolts 160a-d (together "160") is provided to secure the stacked vertical plates 150a-b and 150c-d to the horizontal plates 110a and 110b respectively. In some embodiments, the horizontal plate 110b may not be required while in other embodiments there can be more than two horizontal plates. Square bolt 160 is as described with reference to FIGS. 1C and 1s therefore, not repeated herein for brevity.

A second set of square bolts 260a and 260b (together "260") is provided to secure the vertical plates to horizontal plate 110c for spondylolisthesis reduction. An exemplary square bolt 260 is illustrated in FIG. 2B. The square bolt 260 includes a post 270 and a square-shaped head 272. The post 270 includes a non-threaded portion 276, a first threaded portion 274a, a second threaded portion 274b and a waist portion 266 separating the first and second threaded portions. The second threaded portion 274b—that is the portion 274b above the waist portion 266—is configured to be broken or snapped, when necessary. The combined length of the first threaded portion 274a and the non-threaded portion 276 is around 25%-35% greater than that of equivalent prior art bolts. In one embodiment, the combined length of the first threaded portion 274a and the non-threaded portion 276 is around 17.1 mm. The square-shaped head 272 further includes an opposing pair of protrusions 278a, b ("278"). The protrusions 278 are dimensioned so that they can engage the outside edges of each horizontal plate. A nut 28 can be threaded onto the post 270 of square bolt 260 and tightened. In certain embodiments, the non-threaded portion 276 of the square bolt may include a belt-like protuberance 280 which can function to retain the square bolt in a groove of the through-hole 111f of the horizontal plate 110c without the square bolt 260 falling out of the horizontal plate 110c. The square bolt 260 is configured to be slidably moved within the through-hole 111f of the horizontal plate 110c.

A method of facilitating spondylolisthesis reduction involves providing the spinal implant 200. In the operating theater, vertical plate 150a is stacked over vertical plate 150b and vertical plate 150c is stacked over vertical plate 150d. The first pair of stacked vertical plates 150a-b is placed over the horizontal plates 110a-b proximal to the end 120a. The second pair of stacked plates 150c-d is placed over the horizontal plates 110a-b proximal to the end 120b.

The first and second pair of stacked plates are positioned parallel to each other over the horizontal plates. The through-holes of the vertical plates are positioned above the through-holes of the horizontal plates forming a contiguous opening for bolts 160. Each of the stacked vertical plates is configured to be individually bendable. In some embodiments, there can be more pairs of vertical plates along side 150a-b and 150c-d.

The square bolts are configured to slide along the through-holes 111a-f of the horizontal plates to form a straight line to accommodate the straight vertical plates. Each of the stacked vertical plates can be bent to a desired degree of lumbar lordosis before affixing it to the horizontal plates.

A square bolt 160a is pushed upward from the base of a through-hole in the horizontal plate 110a. The non-threaded portion 176 of the square bolt is retained within the through-holes of the horizontal plate and the through-holes of a first pair of stacked vertical plates 150a-b. The threaded portion 174 of each square bolt passes upwardly through the through-holes of the horizontal and stacked vertical plates where it can be secured with the nut 28 and tightened. Similarly, the remaining square bolts 160b-d are pushed or pressed into the horizontal plates 110a-b to securely couple the vertical stacked plates to horizontal plates.

Square bolts 260a and 260b are also pushed upward from the base of a through-hole in the horizontal plate 110c through the through-holes in the stacked vertical plates 150a-b and 150c-d where they can be secured with nuts 28 and tightened to facilitate spondylolisthesis reduction.

The method involves lifting the listhetic vertebrae upwards and back into normal alignment by forcing the stacked vertical plates 150a-d down onto the listhetic vertebrae using the square bolts 260a and 260b. After alignment, the second threaded portion 274b—that is the portion above the waist portion 274b—of square bolts 260a and 260b is then broken off.

The square bolts 260a and 260b are substantially longer than conventional bolts to accommodate the heights of the stacked vertical plates. The extra-long square bolts ensure that the stacked vertical plates are securely coupled to the horizontal plates.

Immense tension is normally placed on a vertical level due to the spondylolisthesis. The stacking of the vertical plates resists the tension on the vertical level and facilitates strengthening of the spinal implant without compromising on its ability to maintain spinal curvature.

The square bolts, horizontal plates and vertical plates can be comprised of a resilient, bio-inert/biocompatible material that allows passage of the square bolt upwardly through oval through-holes in the horizontal plate and stacked vertical plates but resists passage back in the other direction so that the square bolt does not fall out of the through-holes. In some embodiments, the plates may be made of titanium. Titanium has been observed to possess shape memory/recoil feature that facilitates gradually pulling the listhetic vertebral body back into normal alignment even if complete reduction is not achieved at the time of surgery.

In another embodiment, a method for extending spinal fusion by extension of instrumentation (spinal implant) is disclosed. The third embodiment is indicated generally by reference numeral 300.

During spinal fusion, a first spinal implant 300a is provided. The first spinal implant 300a includes horizontal plates 310a-c ("310") and vertical plates 350a-b ("350"). Horizontal plates 310 are similar to horizontal plates 110 and vertical plates 350 are similar to vertical plates 150 (with the exception that these are not stacked). The features of the horizontal and vertical plates are as disclosed earlier and, are therefore, not repeated herein for brevity. The first spinal implant 300a includes square bolts 360a-f (together "360"). The square bolts 360 are used to affix vertical plates 350a and 350b to the horizontal plates 310a-c. (In some embodiments, it can be just two plates and in others it can be more than three plates). Square bolt 360 is as described with reference to square bolt 160 FIGS. 1C and 1s therefore, not repeated herein for brevity. The square bolts 360 are tightened with nuts 328.

Figure 3B:
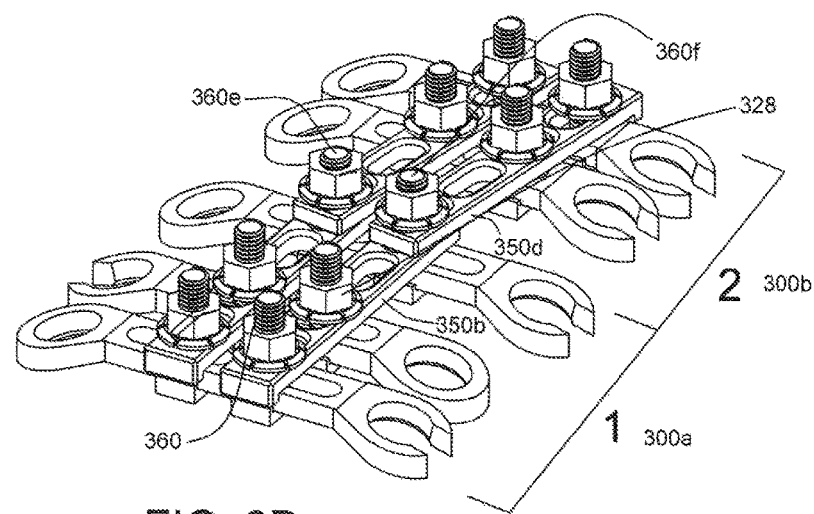
FIGS. 3A and 3B illustrate extension of an original spinal fusion in accordance with another embodiment of the invention.
Figure 3A:
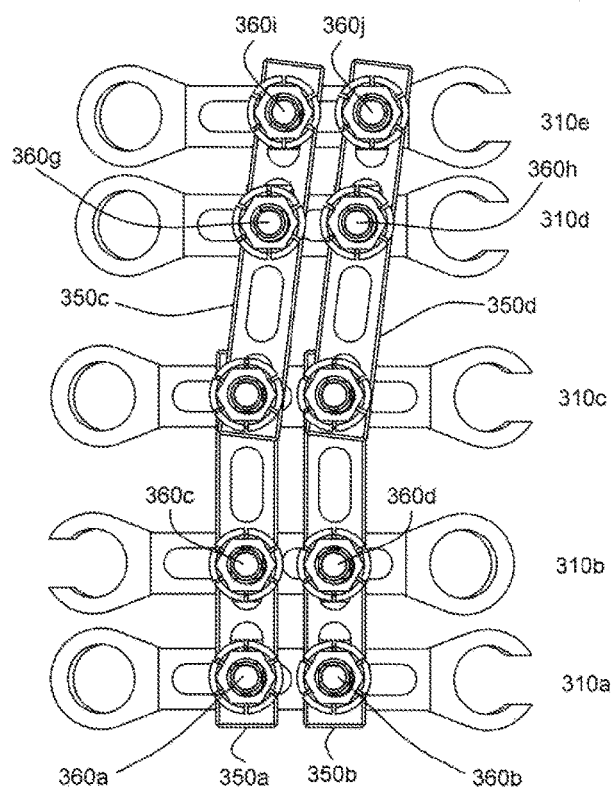

In case of junctional stenosis, or other problems requiring extension of fusion, a second spinal implant 300b is provided. The second spinal implant 300b includes horizontal plates 310c-d and vertical plates 350c-d. However, it is understood that the second spinal implant may include only one level—that is just one horizontal plate 310c or it can include more than three levels—that is, it can further include plates 310f,g, h . . . (not shown). The square bolt 360e is used to stack and couple vertical plate 350a to vertical plate 350c and these stacked vertical plates to the last horizontal plate 310a of the original fusion 300a. The square bolt 360f is used to stack and couple vertical plates 350b to 350d and the stacked vertical plates to the last horizontal plate 310b of the original fusion 300a. Similarly, square bolts 360g-j are used to secure plates 310c and 310d to plates 310d and 310e. Square bolts 360g-j are similar to square bolt 160 as described with reference to FIG. 1C and their features are therefore, not repeated herein for brevity. The square bolts 360 are tightened with nuts 328. As seen in FIG. 3B, the square bolts 360 will stick out at all levels with the exception of square bolts 360e and 360f.

The method for extending fusion involves placing vertical plates 350c and 350d on top of vertical plates 350a and 350b respectively and tightening the bolts 360e and 360f with nuts without exposing or removing the previous instrumentation (such as, spinal implant 300a). The extra length of square bolts 360 facilitate, therefore, facilitate extension of vertical plates above (or below) an existing fusion making extension of instrumentation extremely easy. The extra long square bolts also facilitate angulation of segments of vertical plates in cases of major curvatures from scoliosis and can be extended in multiple segments with multiple junctions without compromising the stability.

In yet another embodiment, a kit containing one or more horizontal plates, vertical plates and square bolts (160, 360 and/or 260) is provided. The kit can also include one or more tightening nuts and other screws required for a spinal implant procedure.

For simplicity of explanation, the methodologies are described herein as a series of acts. It is to be understood and appreciated that the subject innovation is not limited by the acts illustrated and/or by the order of acts, for example acts can occur in various orders and/or concurrently, and with other acts not presented and described herein. Furthermore, not all acts can be required to implement the methodologies in accordance with the disclosed subject matter. The terms "a" or "an" as used herein are to describe elements and components of the invention. This is done merely for convenience and to give a general sense of the invention. The description herein should be read to include one or at least one and the singular also includes the plural unless indicated to the contrary. The term "comprises", "comprising", "includes", "including", "as", "having", or any other variation thereof, are intended to cover non-exclusive inclusions. For example, a process, method, article or apparatus that comprises a list of elements is not necessarily limited to only those elements but may include other elements not expressly listed or inherent to such process, method, article, or apparatus. What has been described above include mere examples of systems and methods. It is, of course, not possible to describe every conceivable combination of components or methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

All modifications which do not depart from the spirit of the present invention, are intended to fall within the scope of the following claims. The terms in the claims have their plain, ordinary meaning unless otherwise explicitly and clearly defined by the patentee. If there is any conflict in the usages of a word or term in this specification and one or more patent(s) or other documents that may be incorporated herein by reference, the definitions that are consistent with this specification should be adopted. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. it is expressly intended that all combinations of those elements that perform substantially the same function in substantially the same way to achieve the same results are within the scope of the invention. Substitutions of elements or steps from one described embodiment to another are also fully intended and contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A spondylolisthesis reduction kit consisting of:
a plurality of horizontal plates comprising at least a first horizontal plate and a second horizontal plate, each of the horizontal plates has a bone facing surface, an opposite upper surface and a plurality of oval-shaped through-holes extending therethrough from the upper surface to the bone facing surface, wherein each of the horizontal plates is configured to be positioned across a vertebral body;
a plurality of vertical plates comprising a pair of a first vertical plate and a second vertical plate, each of the vertical plates has a top surface, a bottom surface, a plurality of oval-shaped through-holes extending therethrough from the top surface to the bottom surface and a lip depending downward from an end of the plate below the bottom surface of the plate;
wherein the first vertical plate is configured to be stacked over the second vertical plate such that the bottom surface of the first vertical plate removably abuts the top surface of the second vertical plate, and wherein the stacked vertical plates are configured to be positioned over a plurality of vertebral bodies;
wherein the first horizontal plate is positioned along a perpendicular axis to the stacked first and second vertical plates;

a first set of square bolts, each of the bolts in the first set of square bolts includes:
  a square-shaped head configured to abut the bone facing surface of the first horizontal plate to prevent rotation of the bolt relative to the first horizontal plate;
  a post extending from the square-shaped head dimensioned to pass through one of the oval-shaped through-holes of the first horizontal plate and through one of the oval-shaped through-holes of the first vertical plate and one of the oval-shaped through-holes of the second vertical plate, the post includes:
    a non-threaded portion proximal to the square-shaped head,
    a first threaded portion proximal to the non-threaded portion,
    a nut having internal threads configured to engage with the first threaded portion for securing the first horizontal plate to the stacked vertical plates adjacent to a first vertebral body;
wherein the first and second stacked vertical plates are configured to be bent to a desired degree of a lumbar lordosis before they are securely coupled to the first horizontal plate with the first set of square bolts;
a second set of square bolts, each of the bolts in the second set of square bolts includes:
  a square-shaped head configured to abut the bone facing surface of the second horizontal plate to prevent rotation of the bolt relative to the second horizontal plate;
  a post extending from the square-shaped head dimensioned to pass through one of the oval-shaped through-holes of the second horizontal plate and through another one of the oval-shaped through-holes of the first vertical plate and another one of the oval-shaped through-holes of the second vertical plate, the post includes:
    a non-threaded portion proximal to the square-shaped head,
    a first threaded portion proximal to the non-threaded portion,
    a second threaded portion proximal to the first threaded portion,
    a non-threaded waist portion separating the first threaded portion form the second threaded portion,
    a nut having internal threads configured to engage with the first and second threaded portions for securing the second horizontal plate to the stacked vertical plates adjacent to a second vertebral body;
wherein a combined length of each of the second set of square bolts is greater than a combined length of each of the first set of square bolts,
wherein the second horizontal plate is configured to be positioned parallel to the first horizontal plate,
wherein the second horizontal plate is located at a different plane than the first horizontal plate to facilitate spondylolisthesis reduction; and
wherein the combined length of each bolt of the first set of square bolts is about 17.1 mm to facilitate coupling the first horizontal plate to the stacked first and second vertical plates, and the combined length of each bolt of the second set of square bolts is greater than 17.1 mm.

2. The kit according to claim 1, wherein the second threaded portion is configured to be broken off.

3. A spinal implant kit consisting of:
  a plurality of horizontal plates comprising at least a first horizontal plate and a second horizontal plate, each of the horizontal plates has a bone facing surface, an opposite upper surface and a plurality of oval-shaped through-holes extending therethrough from the upper surface to the bone facing surface, wherein each of the horizontal plates is configured to be positioned across a vertebral body;
  a plurality of vertical plates comprising a pair of a first vertical plate and a second vertical plate, each of the vertical plates has a top surface, a bottom surface, a plurality of oval-shaped through-holes extending therethrough from the top surface to the bottom surface and a lip depending downward from an end of the plate below the bottom surface of the plate;
  wherein the first vertical plate is configured to be stacked over the second plate such that the bottom surface of the first vertical plate removably abuts the top surface of the second vertical plate, and wherein the stacked vertical plates are configured to be positioned over a plurality of vertebral bodies;
  wherein the first horizontal plate is positioned along a perpendicular axis to the stacked first and second vertical plates;
  a first set of square bolts, each of the bolts in the first set of square bolts includes:
    a square-shaped head configured to abut the bone facing surface of the first horizontal plate to prevent rotation of the bolt relative to the first horizontal plate;
    a post extending from the square-shaped head dimensioned and configured to pass through the oval-shaped through-holes of the first and second horizontal plates and through the oval-shaped through-holes of the first vertical plate and the oval-shaped through-holes of the second vertical plate, the post includes:
      a non-threaded portion proximal to the square-shaped head,
      a first threaded portion proximal to the non-threaded portion,
      a nut having internal threads configured to engage with the first threaded portion for securing the first and second horizontal plates to the stacked vertical plates adjacent to first and second vertebral bodies;
  wherein the first and second stacked vertical plates are configured to be bent to a desired degree of a lumbar lordosis before they are securely coupled to the horizontal plates with the first set of square bolts;
  wherein the combined length of each bolt of the first set of square bolts is about 17.1 mm or longer to facilitate coupling the first horizontal plate to the stacked first and second vertical plates.

4. The kit according to claim 3, wherein the spinal implant is formed of a biocompatible material.

5. The kit according to claim 4, wherein the biocompatible material is titanium.

* * * * *